(12) United States Patent
Lago

(10) Patent No.: US 6,448,272 B1
(45) Date of Patent: Sep. 10, 2002

(54) MYT1 KINASE INHIBITORS

(75) Inventor: Maria A. Lago, Audubon, PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/857,519

(22) PCT Filed: Dec. 7, 1999

(86) PCT No.: PCT/US99/28990

§ 371 (c)(1), (2), (4) Date: Jul. 19, 2001

(87) PCT Pub. No.: WO00/33841

PCT Pub. Date: Jun. 15, 2000

Related U.S. Application Data

(60) Provisional application No. 60/111,328, filed on Dec. 7, 1998.

(51) Int. Cl.[7] .................. A61K 31/4439; C07D 277/38; C07D 417/12
(52) U.S. Cl. ...................... 514/333; 514/370; 546/256; 548/198
(58) Field of Search .................................. 514/333, 370; 546/256; 548/198

(56) References Cited

U.S. PATENT DOCUMENTS 5,908,931 A * 6/1999 Rajagopalan et al.

OTHER PUBLICATIONS

Database CAOLD on STN, AN CA58:6167h. UNO et al. 'Thiazole Derivatives as analog Reagents—(VII) Reaction of 4,4'–Bithiazole Derivatives with Metal Ions'. Bunseki Kagaku, 1961, vol. 10, pp. 750–755.

Database CAOLD on STN, AN CA58:3410f. UNO et al. Thiazole Derivatives as analog Reagents—(V) 4,4'–Bithiazole Derivatives. Yakugaku Zasshi, 1962, vol. 82, pp. 257–260.

Database CAPLUS on STN, AN 1967:37814. Roocker et al. 'Preparation of New Bis(4–thiaxolyl0benzens'. Bull. Soc. Chim. Belg. 1966, vol. 75, Nos. 9–10, pp. 641–647.

Mbagwu, et al.. Some Novel Mesoionic Bispurinone analogs: Studies on Preparation and Characterization. J. Heterocycl. Chem. Mar.–Apr. 1988, vol. 25, No. 2, pp. 571–573.

Patnaik, B.K., "Polythiazoles", *Journal of Polymer Science*, vol. 7, 1969, pp. 3407–3412, XP001057057, p. 3407.

* cited by examiner

*Primary Examiner*—Ceila Chang
(74) *Attorney, Agent, or Firm*—Soma G. Simon; Mary E. McCarthy; Charles M. Kinzig

(57) ABSTRACT

A compound according to Formula (I), hereinbelow:

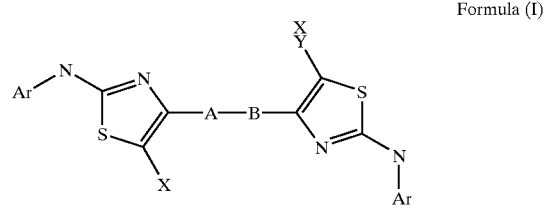

Formula (I)

wherein A—B represents a covalent bond or an optionally substituted 1,3 or 1,4 aryl ring selected from the group consisting of:

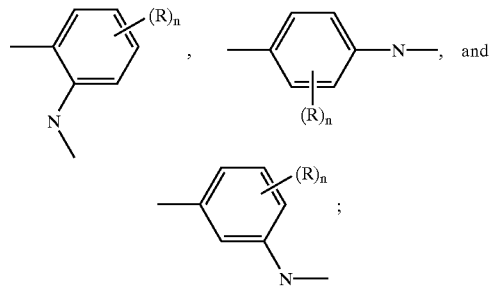

X is independently selected from the group consisting of H, Br, $CH_3$, CN, and $NR_1R_2$, wherein $R_1$ and $R_2$ represent hydrogen or $C_{1-4}$ alkyl; branched or cyclic, optionally containing O or N; and Ar represents optionally substituted phenyl or an optionally substituted 5 or 6 membered heterocylic ring containing one or more heteroatoms selected from N, O and S;

provided that when Y is hydrogen, at least one Ar contains a heteroatom selected from N, S and O.

6 Claims, No Drawings

MYT1 KINASE INHIBITORS

This application is a 371 of PCT/US99/28990 filed Dec. 7, 1999 which claims the benefit of provisional application No. 60/111,328 filed Dec. 7 1998.

FIELD OF THE INVENTION

The present invention relates to membrane-associated tyrosine and threonine kinase ("myt1 kinase") enzyme inhibitors, pharmaceutical compositions comprising these compounds and methods for identifying these compounds and methods of using these compounds to treat various forms of cancer and hyperproliferative diseases.

BACKGROUND OF THE INVENTION

Entry into mitosis is initiated by the M phase-promoting factor (MPF), a complex containing the cdc2 protein kinase and cyclin B. Proper regulation of MPF ensures that mitosis occurs only after earlier phases of the cell cycle are complete. Phosphorylation of cdc2 at Tyr-15 and Thr-14 suppresses this activity during interphase (G1, S, and G2). At G2-M transition, cdc2 is dephosphorylated at Tyr-15 and Thr-14 allowing MPF to phosphorylate its mitotic substrates. A distinct family of cdc-regulatory kinases (Wee1) is known to be responsible for phosphorylation of the cdc Tyr-15. A new member of this family, Myt1 was recently described as the Thr-14 and Tyr-15-specific cdc2 kinase, and shown to be an important regulator of cdc2/cyclin B kinase activity (Science 270:86–90, 1995; Mol. Cell. Biol. vol 17:571, 1997). The inhibitory phosphorylation of cdc2 is important for the timing of entry into mitosis. Studies have shown that premature activation of cdc2 leads to mitotic catastrophe and cell death. Inhibition of Myt1 is predicted to cause premature activation of cdc2, and thus would kill rapidly proliferating cells. In addition, Myt1 inhibition is predicted to reduce resistance to conventional DNA-damaging chemotherapeutics, because the mechanisms by which cells avoid death involve arrest in the G2 phase of the cell cycle, and repair or DNA damage prior to division. That arrest should be prevented by blocking Myt1 inhibitory phosphorylation of cdc2. Thus forcing the cell to enter mitosis prematurely.

Myt1 kinase is an important cell cycle regulator, particularly at the G2/M phase. Inhibitors would therefore be attractive for the treatment of cancer. Current cancer therapies, including surgery, radiation, and chemotherapy, are often unsuccessful in curing the disease. The patient populations are large. For example, in colon cancer alone there are 160,000 new cases each year in the US, and 60,000 deaths. There are 600,000 new colon cancer cases each year worldwide. The number for lung cancer is twice that of colon cancer. The largest deficiency of chemotherapies for major solid tumors is that most patients fail to respond. This is due to cell cycle regulation and subsequent repair of damage to DNA or mitotic apparatus, the targets for most effective chemotherapeutic agents. Myt1 kinase offers a point of intervention downstream from these mechanisms by which tumor cells develop resistance. Inhibition of Myt1 could in and of itself have therapeutic benefit in reducing tumor proliferation, and in addition, could be used in conjunction with conventional chemotherapies to overcome drug resistance.

Based on the foregoing, there is a need to identify a potent myt1 kinase enzyme inhibitor for the treatment of various indications, including cancer, associated with the present receptor.

SUMMARY OF THE INVENTION

The present invention involves compounds represented by Formula (I) hereinbelow, pharmaceutical compositions comprising such compounds and methods of antagonizing the myt1 kinase receptor using these compounds.

DETAILED DESCRIPTION OF THE INVENTION

The present invention provides compounds of Formula (I), hereinbelow:

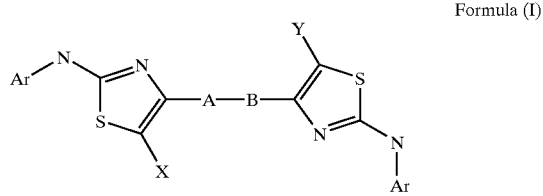

Formula (I)

wherein A—B represents a covalent bond or an optionally substituted 1,3 or 1,4 aryl ring selected from the group consisting of:

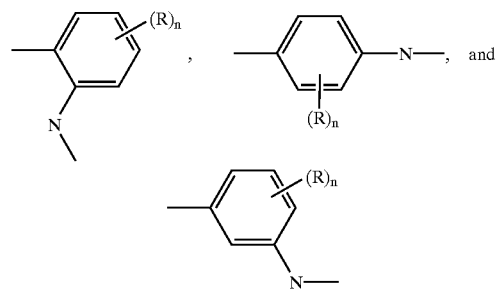

X is independently selected from the group consisting of H, Br, $CH_3$, CN, and $NR_1R_2$, wherein $R_1$ and $R_2$ represent hydrogen or $C_{1-4}$ alkyl; branched or cyclic, optionally containing O or N; and Ar represents optionally substituted phenyl or an optionally substituted 5 or 6 membered heterocylic ring containing one or more heteroatoms selected from N, O and S; provided that when Y is hydrogen, at least one Ar contains a heteroatom selected from N, S and O.

Preferred aryl substituents are selected from the group consisting of phenyl, O—$C_{1-4}$ alkyl, halo, nitro, and $NR_1R_2$, wherein $R_1$ and $R_2$ is as defined hereinabove.

Preferred compounds of the present invention are selected from the group consisting of:
1,4-bis(2-phenylamino-4-thiazolyl)benzene,
1-[2-phenyl-4-(5-bromo)thiazolyl]-4-[2-phenyl-4-thiazolyl]benzene,
1,4-bis(2-phenylamino-4-(5-bromo)thiazolyl)benzene,
1,4-bis(2-(3-pyridylamino)-4-thiazolyl)benzene,
1,4-bis(2-phenyl)-(4-(5-bromo)thiazolylbenzene,
1-[(2-(3-pyridylamino)-4-(5-bromo)thiazolyl)]-4-[2-(3-pyridylamino)-4-thiazolyl]benzene,
1,3-bis(2-(3-pyridylamino)-4-thiazolyl)benzene,
1,4-bis(2-(2-pyridylamino)-4-thiazolyl)benzene,
4,4'-di(2-(2-methoxypyrid-5-ylamino)thiazolyl),
4,4'-di(2-(2-pyridylamino)thiazolyl), and
4,4'-Di(2,2-phenylaminothiazolyl).

More preferred compounds of the present invention are selected from the group consisting of:
1,4-bis(2-phenylamino-4-thiazolyl)benzene, 1-[2-phenyl4-(5-bromo)thiazolyl]-4-[2-phenyl-4-thiazolyl]
   benzene,
1,4-bis(2-phenylamino-4-(5-bromo)thiazolyl)benzene,
1,4-bis(2-(3-pyridylamino)-4-thiazolyl)benzene,
1-[(2-(3-pyridylamino)-4-(5-bromo)thiazolyl)]-4-[2-(3-
   pyridylamino)4-thiazolyl]benzene,
1,3-bis(2-(3-pyridylamino)-4-thiazolyl)benzene,
4,4'-di(2-(2-methoxypyrid-5-ylamino)thiazolyl),
1,4-bis(2-(2-pyridylamino)-4-thiazolyl)benzene, and
4,4'-di(2-2-pyridylaminothiazolyl).

The most preferred compounds useful in the present invention are selected from the group consisting of:
1,4bis(2-phenylamino-4-thiazolyl)benzene 1-[2-phenyl-4-
   (5-bromo)thiazolyl]-4-[2-phenyl-4-thiazolyl]benzene,
1,4-bis(2-phenylamino-4-(5-bromo)thiazolyl)benzene,
1,4-bis(2-(3-pyridylamino)-4-thiazolyl)benzene
1-[(2-(3-pyridylamino)-4-(5-bromo)thiazolyl)]-4-[2-(3-
   pyridylamino)-4-thiazolyl]benzene
1,4-bis(2-(2-pyridylamino)-4-thiazolyl)benzene 1,3-bis(2-
   (3-pyridylamino)-4-thiazolyl)benzene and
4,4'-di(2-(2-pyridylamino)thiazolyl).

As used herein, "alkyl" refers to an optionally substituted hydrocarbon group joined together by single carbon-carbon bonds. The alkyl hydrocarbon group may be linear, branched or cyclic, saturated or unsaturated. Preferably, the group is saturated linear or cyclic.

The compounds of the present invention may contain one or more asymmetric carbon atoms and may exist in racemic and optically active forms. All of these compounds and diastereomers are contemplated to be within the scope of the present invention.

The present compounds can also be formulated as pharmaceutically acceptable salts and complexes thereof. Pharmaceutically acceptable salts are non-toxic salts in the amounts and concentrations at which they are administered.

Preferred salts inclure dihydrobromide, dihydrochloride, hydrobromide and bistrifluroacetate. Pharmaceutically acceptable salts include acid addition salts such as those containing sulfate, hydrochloride, fumarate, maleate, phosphate, sulfamate, acetate, citrate, lactate, tartrate, methanesulfonate, ethanesulfonate, benzenesulfonate, p-toluenesulfonate, cyclohexylsulfamate and quinate. Pharmaceutically acceptable salts can be obtained from acids such as hydrochloric acid, maleic acid, sulfuric acid, phosphoric acid, sulfamic acid, acetic acid, citric acid, lactic acid, tartaric acid, malonic acid, methanesulfonic acid, ethanesulfonic acid, benzenesulfonic acid, p-toluenesulfonic acid, cyclohexylsulfamic acid, fumaric acid, and quinic acid.

Pharmaceutically acceptable salts also include basic addition salts such as those containing benzathine, chloroprocaine, choline, diethanolamine, ethylenediamine, meglumine, procaine, aluminum, calcium, lithium, magnesium, potassium, sodium, ammonium, alkylamine, and zinc, when acidic functional groups, such as carboxylic acid or phenol are present.

The present compounds are readily prepared by the schemes represented below:

Scheme 1

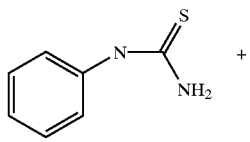

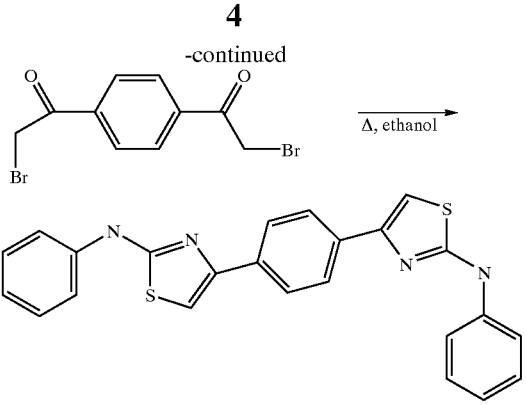

Scheme 2

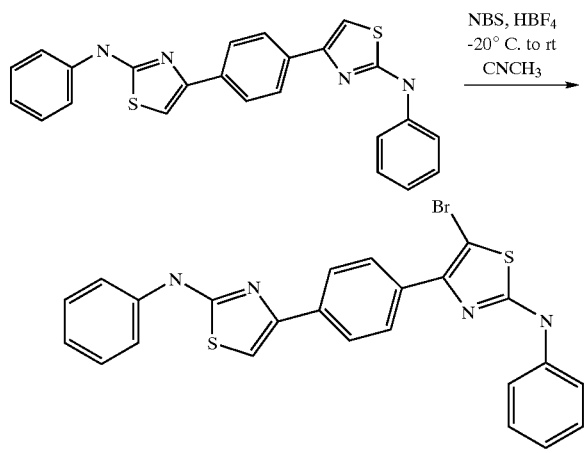

Scheme 3

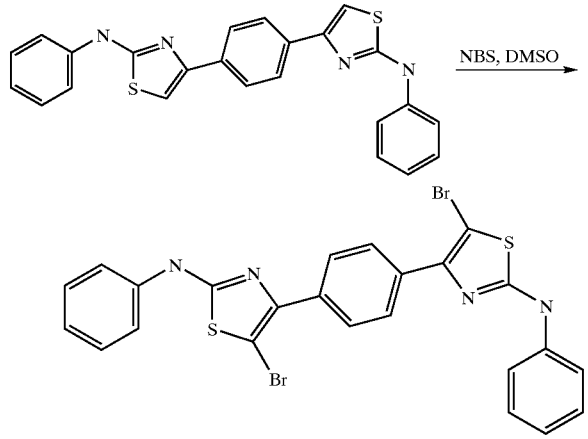

The general procedure for the synthesis of this compounds is illustrate in Scheme 1 for the synthesis of 1,4-bis (2-phenylamino-4-thiazolyl)benzene dihydrobromide. The corresponding bisthiazolyl compounds are synthesized via condensation of the bis bromoketones with two equivalents of a suitably substituted thiourea. The reagents are dissolved in a solvent such as ethanol, isopropanol or any other suitable solvent, the reaction mixture is heated to 70–90° C. for several hours (4–12 h). Cooling of the reaction yields de desired product as a bis-hydrobromide salt. Monobromination of the bisthiazole compounds can be accomplish for example via the reaction of N-bromosuccinimide in the presence of an acid such as Fluoroboric acid, or any other suitable protic acid, in a solvent such as acetonitrile or any other suitable solvent, following a procedure described in the literature (Oberhauser, T. *J.Org. Chem.*, 1997, 62, 4504–4506). Bis-bromination can be accomplish via any known bromination reaction, such as reaction of the bis-thiazole with N-bromosuccinimide in refluxing DMSO or acetonitrile or Bromine in acetic acid or any other method known to chemists skilled in the art.

With appropriate manipulation and protection of any chemical functionality, synthesis of the remaining compounds of Formula (I) is accomplished by methods analogous to those above.

In order to use a compound of Formula (I) or a pharmaceutically acceptable salt thereof for the treatment of humans and other mammals, it is normally formulated in accordance with standard pharmaceutical practice as a pharmaceutical composition.

The present ligands can be administered by different routes including intravenous, intraperitoneal, subcutaneous, intramuscular, oral, topical, transdermal, or transmucosal administration. For systemic administration, oral administration is preferred. For oral administration, for example, the compounds can be formulated into conventional oral dosage forms such as capsules, tablets and liquid preparations such as syrups, elixirs and concentrated drops.

Alternatively, injection (parenteral administration) may be used, e.g., intramuscular, intravenous, intraperitoneal, and subcutaneous. For injection, the compounds of the invention are formulated in liquid solutions, preferably, in physiologically compatible buffers or solutions, such as saline solution, Hank's solution, or Ringer's solution. In addition, the compounds may be formulated in solid form and redissolved or suspended immediately prior to use. Lyophilized forms can also be produced.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, bile salts and fusidic acid derivatives. In addition, detergents may be used to facilitate permeation. Transmucosal administration, for example, may be through nasal sprays, rectal suppositories, or vaginal suppositories.

For topical administration, the compounds of the invention can be formulated into ointments, salves, gels, or creams, as is generally known in the art. The amounts of various compounds to be administered can be determined by standard procedures taking into account factors such as the compound $IC_{50}$, $EC_{50}$, the biological half-life of the compound, the age, size and weight of the patient, and the disease or disorder associated with the patient. The importance of these and other factors to be considered are known to those of ordinary skill in the art.

Amounts administered also depend on the routes of administration and the degree of oral bioavailability. For example, for compounds with low oral bioavailability, relatively higher doses will have to be administered.

Preferably the composition is in unit dosage form. For oral application, for example, a tablet, or capsule may be administered, for nasal application, a metered aerosol dose may be administered, for transdermal application, a topical formulation or patch may be administered and for transmucosal delivery, a buccal patch may be administered. In each case, dosing is such that the patient may administer a single dose.

Each dosage unit for oral administration contains suitably from 0.01 to 500 mg/Kg, and preferably from 0.1 to 50 mg/Kg, of a compound of Formula (I) or a pharmaceutically acceptable salt thereof, calculated as the free base. The daily dosage for parenteral, nasal, oral inhalation, transmucosal or transdermal routes contains suitably from 0.01 mg to 100 mg/Kg, of a compound of Formula(I). A topical formulation contains suitably 0.01 to 5.0% of a compound of Formula (I). The active ingredient may be administered from 1 to 6 times per day, preferably once, sufficient to exhibit the desired activity, as is readily apparent to one skilled in the art.

As used herein, "treatment" of a disease includes, but is not limited to prevention, retardation and prophylaxis of the disease. As used herein, "diseases" treatable using the present compounds include, but are not limited to leukemias, solid tumor cancers, metastases, soft tissue cancers, brain cancer, esophageal cancer, stomach cancer, pancreatic cancer, liver cancer, lung cancer, bladder cancer, bone cancer, prostate cancer, ovarian cancer, cervical cancer, uterine cancer, testicular cancer, kidney cancer, head cancer and neck cancer, chronic inflammatory proliferative diseases such as psoriasis and rheumatoid arthritis; proliferative cardiovascular diseases such as restenosis; proliferative ocular disorders such as diabetic retinopathy; and benign hyperproliferative diseases such as hemangiomas.

Composition of Formula (I) and their pharmaceutically acceptable salts which are active when given orally can be formulated as syrups, tablets, capsules and lozenges. A syrup formulation will generally consist of a suspension or solution of the compound or salt in a liquid carrier for example, ethanol, peanut oil, olive oil, glycerine or water with a flavoring or coloring agent. Where the composition is in the form of a tablet, any pharmaceutical carrier routinely used for preparing solid formulations may be used. Examples of such carriers include magnesium stearate, terra alba, talc, gelatin, acacia, stearic acid, starch, lactose and sucrose. Where the composition is in the form of a capsule, any routine encapsulation is suitable, for example using the aforementioned carriers in a hard gelatin capsule shell. Where the composition is in the form of a soft gelatin shell capsule any pharmaceutical carrier routinely used for preparing dispersions or suspensions may be considered, for example aqueous gums, celluloses, silicates or oils, and are incorporated in a soft gelatin capsule shell.

Typical parenteral compositions consist of a solution or suspension of a compound or salt in a sterile aqueous or non-aqueous carrier optionally containing a parenterally acceptable oil, for example polyethylene glycol, polyvinylpyrrolidone, lecithin, arachis oil or sesame oil.

Typical compositions for inhalation are in the form of a solution, suspension or emulsion that may be administered as a dry powder or in the form of an aerosol using a conventional propellant such as dichlorodifluoromethane or trichlorofluoromethane.

A typical suppository formulation comprises a compound of Formula (I) or a pharmaceutically acceptable salt thereof which is active when administered in this way, with a binding and/or lubricating agent, for example polymeric glycols, gelatins, cocoa-butter or other low melting vegetable waxes or fats or their synthetic analogs.

Typical dermal and transdermal formulations comprise a conventional aqueous or non-aqueous vehicle, for example a cream, ointment, lotion or paste or are in the form of a medicated plaster, patch or membrane.

Preferably the composition is in unit dosage form, for example a tablet, capsule or metered aerosol dose, so that the patient may administer a single dose.

No unacceptable toxological effects are expected when compounds of the present invention are administered in accordance with the present invention.

The biological activity of the compounds of Formula (1) are demonstrated by the tests indicated hereinbelow.

In Vitro Assays

Compounds capable of inhibiting myt 1 kinase can be identified with in vitro assays and cellular assays as described below. Variations of these assays would be obvious to those skilled in the art.

Expression of GST-Myt1

A GST-Myt1 expression construct was constructed which has the glutathione-S-transferase gene fused to the amino terminus of Myt1 kinase via a linker containing a thrombin cleavage site. This clone has been truncated at amino acid 362 of Myt1, just prior to the to the transmembrane domain. This construct was cloned into the Baculovirus expression vector, pFASTBAC, and this was used to make the viral stock for the subsequent infection. Spodoptera frugiperda cells (Sf21) were infected with the virus expressing the GST-Myt1 and the cells were grown for 3 days, then harvested and frozen down.

Purification of GST-Myt1

The GST-Myt1 protein was purified as follows: An Sf21 cell pellet expressing GST-Myt1 was resuspended on ice in 10 mls of lysis buffer (50 mM Tris-Cl, pH 7.5, 250 mM $NaCl_2$, 1 mM dithiothreitol (DTT), 0.1% NP-40, 5% (v/v) protease inhibitor cocktail, 1 mM sodium orthovanadate), cells were lysed by sonication and centrifuged at 100,000×g for 30 min. The supernatant was added to 5 mls (packed volume) of Glutathione Sepharose 4B, equilibrated in wash buffer (20 mM Tris-Cl, pH 7.0, 10 mM $MgCl_2$, 100 mM $NaCl_2$, 1 mM DTT, 0.5%(v/v) protease inhibitor cocktail, 1 mM sodium orthovanadate). The mixture was rocked for 30 min. The resin with the bound GST-Myt1 was spun down at 500×g for 5min and washed with 14 mls of wash buffer. The beads were spun as above and resuspended in another 14 mls of wash buffer. The suspension was transferred into a column and allowed to pack, then the wash buffer was allowed to flow through by gravity. The GST-Myt1 was eluted from the column with 10 mls of 10 mM Glutathione in 50 mM Tris-Cl, pH 8.0 in 500 ul fractions. Protein concentrations were determined on the fractions using Bio-Rad's Protein assay kit as per instructions. Fractions containing the GST-Myt1 were pooled and diluted to a concentration of ~0.5 mg/ml and dialyzed for 4 hours at 4° C. in dialysis buffer (20 mM HEPES, pH 7.0, 1 mM Manganese Acetate, 100 mM $NaCl_2$, 0.05% Brij-35, 10% glycerol, 1 mM DTT, 0.2% (v/v) protease inhibitor cocktail, 1 mM sodium orthovanadate). The protein was aliquoted and stored at −80°.

Enzyme Assays

GST-Myt1 autophosphorylation-DELFIA Assay

Delayed fluorescent immunoassays (DELFIA) were performed in 96 well NUNC maxisorp plates, at 50 ul/well with 0.25 ug GST-Myt1, in BufferA (50 mM HEPES, pH 7.4, 2 mM $Mn(OAc)_2$, 5 uM ATP, 1 mM DTT). For determination of pH optimum, divalent cation usage and $K_m$ of ATP, the appropriate component was varied as indicated in the figures. Autophosphorylation reactions were initiated by the addition of GST-Myt1 in buffer and were allowed to proceed at room temperature with shaking for 20 min. The reactions were stopped with the addition of EDTA to a 20 mM final concentration, and the protein was allowed to continue to bind to the wells for an additional 40 min. Wells were washed three times with 300 ul TBS/Tween (50 mM Tris, pH 7.4, 150 mM $NaCl_2$, 0.2% Tween-20). After washing, the plate was blocked using Pierce's Superblock in TBS at 100 ul/well. This was immediately decanted and the blocking was repeated two more times. The plate was then washed again with three washes of 300 ul/well of TBS-Tween. Then 100 ul of Eu-labeled anti-phosphotyrosine antibody diluted to 0.125 ug/ml in TBS/Tween containing 0.15 mg/ml BSA was added to the wells and allowed to incubate for 30 min with shaking at room temperature. Wells were then washed three times with 300 ul of TBS/Tween, 200 ul of Enhancement solution was added per well and incubated with shaking for 10 min. The plate was then read on the 1420 VICTOR plate counter from Wallac, Inc. The identical conditions are used for inhibitor studies except that ATP is at 1 uM and inhibitors are added, in dimethyl sulfoxide (DMSO) to a final concentration of 1%. Typical concentration ranges in which test compounds are expected to inhibit myt1 autophosphorylation are 0.001 to 10 uM.

Biological Studies

Cell Cycle Studies

Drug studies considering cellular effects were performed in the Hela S3 adherent cell line. Cells were plated at a concentration sufficiently low such that 24 hours later they were at 10–20% confluence (typically $2 \times 10^5$ cells/15cm e3). Cells were then synchronized in S phase by a repeated thymidine block. Briefly, cells were treated with 2 mM thymidine for 18 hours, released for 8 hours by 3 washes, and then treated again with thymidine. Following the second release from thymidine, 95% of cells were in S phase. Synchronized cells were then returned to complete media containing a DNA-damaging drug such as 50 nM topotecan (a dosage we have found to be sufficient to arrest cells in early G2 phase without inducing apoptosis) alone and in combination with test compounds for up to 18 hours. Cell Cycle profiles were then performed cytometrically using a procedure for propidium iodide staining of nuclei. (Vindelov et al, Cytometry Vol.3, No.5, 1983, 323–327) Myt1 inhibitors would be expected to reverse the G2 arrest caused by the DNA damaging agent. Typical concentration ranges for such activity would be 0.001 to 10 uM.

Proliferation/Apoptosis Studies

Proliferation studies were performed in a variety of adherent and non-adherent cell lines including Hela S3, HT29, and Jurkat(delete ***). The proliferation assay utilized a calorimetric change resulting from reduction of the tetrazolium reagent XTT into a formazan product by metabolically active cells (Scudiero et al. Cancer Research, 48, 1981, 4827–4833). Cells were seeded in 100 uls in 96 well plates to roughly 10% confluence (cell concentration varied with cell lines) and grown for 24 hours. Compounds were then added with or without sufficient vehicle-containing media to raise the cells to a 200 ul final volume containing chemical reagents in 0.2% DMSO. Cells received multiple concentrations of DNA-damaging anti-proliferative drugs such as topotecan, test compounds, and combination treatment at 37° C. 5% $CO_2$. 72 hours later, 50 uls of an XTT/phenazine methosulfate mixture were added to each well and cells were left to incubate for 90 mins. Plate was read at 450 nm, and anti-proliferative effects were compared relative to vehicle treated cells. Myt1 inhibitors are expected to inhibit the proliferation of such cancer cell lines and/or enhance the cytotoxicity of DNA-damaging chemotherapeutic drugs. Typical concentration ranges for such activity would be 0.001 to 10 uM. Other assays for cellular proliferation or cytotoxicity could also be used with test compounds, and these assays are known to those skilled in the art. The present invention includes but is not limited to the examples below.

Nuclear magnetic resonance spectra were recorded at 300 MHz using a Bruker AM 300 spectrometer. CDCl$_3$ is deuteriochloroform, DMSO-d$_6$ is hexadeuteriodimethylsulfoxide, and CD$_3$OD is tetradeuteriomethanol. Chemical shifts are reported in parts per million (?) downfield from the internal standard tetramethylsilane. Abbreviations for NMR data are as follows: s=singlet, d=doublet, t=triplet, q=quartet, m=multiplet, dd=doublet of doublets, dt=doublet of triplets, app=apparent, br=broad. J indicates the NMR coupling constant measured in Hertz. Continuous wave infrared (IR) spectra were recorded on a Perkin-Elmer 683 infrared spectrometer, and Fourier transform infrared (FTIR) spectra were recorded on a Nicolet Impact 400 D infrared spectrometer. IR and FTIR spectra were recorded in transmission mode, and band positions are reported in inverse wavenumbers (cm$^{-1}$). Mass spectra were taken on either VG 70 FE, PE Syx API III, or VG ZAB HF instruments, using fast atom bombardment (FAB) or electrospray (ES) ionization techniques. Elemental analyses were obtained using a Perkin-Elmer 240C elemental analyzer. Melting points were taken on a Thomas-Hoover melting point apparatus and are uncorrected. All temperatures are reported in degrees Celsius.

Analtech Silica Gel GF and E. Merck Silica Gel 60 F-254 thin layer plates were used for thin layer chromatography. Both flash and gravity chromatography were carried out on E. Merck Kieselgel 60 (230–400 mesh) silica gel. Analytical and preparative HPLC were carried out on Rainin or Beckman chromatographs. ODS refers to an octadecylsilyl derivatized silica gel chromatographic support. 5µ Apex-ODS indicates an octadecylsilyl derivatized silica gel chromatographic support having a nominal particle size of 5µ, made by Jones Chromatography, Littleton, Colo. YMC ODS-AQ® is an ODS chromatographic support and is a registered trademark of YMC Co. Ltd., Kyoto, Japan. PRP-1® is a polymeric (styrene-divinylbenzene) chromatographic support, and is a registered trademark of Hamilton Co., Reno, Nev.) Celite® is a filter aid composed of acid-washed diatomaceous silica, and is a registered trademark of Manville Corp., Denver, Colo.

EXAMPLE 1

1,4-bis(2-phenylamino-4-thiazolyl)benzene dihydrobromide

MS (ES) m/e 426.8[M+H]$^+$ $^1$H NMR (300 MHz, DMSO-d) ? 8.04(s, 4H), 7.77(d, J=8 Hz, 4H), 7.37(m, 6H), 7.01(t, J=8 Hz, 2H).

EXAMPLE 2

1-[2-phenyl-4-(5-bromo)thiazolyl]-4-[2-phenyl-4-thiazolyl]benzene dihydrochloride MS (ES) m/e 504.5[M+H]$^+$ $^1$H NMR (300 MHz, DMSO-d) ??8.06(dd, J=8,11 Hz, 4H), 7.80(d, J=9 Hz, 2H), 7.69(d, J=11 Hz, 2H), 7.48(s, 1H), 7.38(m, 4H), 7.03(m, 2H)

EXAMPLE 3

1,4-bis(2-phenyl)-(4-(5-bromo)thiazolyl)benzene dihydrochloride

MS (ES) m/e 582.3[M+H]$^+$ $^1$H NMR (300 MHz, DMSO-d) ??8.08(s, 4H), 7.68(d, J=7 Hz, 4H), 7.38(t, J=10 Hz, 4H), 7.06(t, J=7 Hz, 2H)

EXAMPLE 4

1,4-bis(2-(3-pyridylamino)-4-thiazolyl)benzene bistrifluoroacetate

MS (ES) m/e 428.9 [M+H]$^+$ $^1$H NMR (300 MHz, DMSO-d) ??9.24(s, 2H), 8.48(d, J=7 Hz, 2H), 8.42(d, J=4 Hz, 2H), 8.06(s, 4H), 7.76(m, 2H), 7.62(s, 2H)

EXAMPLE 5

1-[(2-(3-pyridylamino)-4-(5-bromo)thiazolyl)]-4-[2-(3-pyridylamino)-4-thiazolyl]benzene bis trifluoroacetate MS (ES) m/e 508.9 [M+H]$^+$ $^1$H NMR (300 MHz, DMSO-d) ??9.26(s, 1H), 9.03(s, 1H), 8.48(d, J=3 Hz, 1H), 8.40(d, J=4 Hz, 1H), 8.32(m, 2H), 8.08(m, 4H), 7.73(m, 1H) 7.63(s, 1H), 7.56(m, 1H)

EXAMPLE 6

1,3-bis(2-(3-pyridylamino)-4-thiazolyl)benzene dihydrobromide

MS (ES) m/e 428.6 [M+H]$^+$

EXAMPLE 7

1,4-bis(2-(2-pyridylamino)-4-thiazolyl)benzene dihydrobromide

MS (ES) m/e 428.8 [M+H]+

EXAMPLE 8

1,3-bis(2-(2-pyridylamino)-4-thiazolyl)benzene dihydrobromide

MS (ES) m/e 428.8 [M+H]$^+$

EXAMPLE 9

4,4'-Di(2,2-phenylaminothiazolyl)dihydrobromide

Some general procedure using 1,4-dibromo-2,3-butenedione (300 mg, 1.23 mmol) and 1-Phenyl-2-thiourea (274 mg, 2.46 mmol) to obtain the title compound (88%) as a pale pink compound.

$^1$H NMR (300 MHz, DMSO-d) ??6.82 (d, J=7.5 Hz, 2H), 6.81 (d, J=7.6 Hz, 2H), 6.66(t, J=7.5 Hz, 4H), 6.46 (s, 2H), 6.43 (t, J=7.7 Hz, 2H).

MS (ES) m/e 351.8 [M+H]$^+$

EXAMPLE 10

4,4'-di(2-(2-methoxypyrid-5-ylamino)thiazolyl) bistrifluoracetate

MS (ES) m/e 412.7 [M+H]$^+$ $^1$H NMR (300 MHz, DMSO-d) ??7.98(s, 2H), 7.34(m, 2H), 6.36(s, 2H), 6.25(d, J=11 Hz, 2H), 3.21(s, 6H)

EXAMPLE 11

4,4'-di(2-(2-pyridyl)aminothiazolyl)bistrifluoracetate

MS (ES) m/e 353.7 [M+H]$^+$ $^1$H NMR (300 MHz, DMSO-d) ??7.76(d, J=7 Hz, 2H), 7.25(t, J=10 Hz, 2H), 6.88(s, 2H), 6.49–6.38(m, 4H)

Formulations for pharmaceutical use incorporating compounds of the present invention can be prepared in various forms and with numerous excipients. Examples of such formulations are given below:

EXAMPLE 12

Inhalant Formulation

A compound of Formula (I), (1 mg to 100 mg) is aerosolized from a metered dose inhaler to deliver the desired amount of drug per use.

EXAMPLE 13

Tablet Formulation:

| Tablets/Ingredients | Per Tablet |
|---|---|
| 1. Active Ingredient (Cpd of Form. (I) | 40 mg |
| 2. Corn Starch | 20 mg |
| 3. Alginic acid | 20 mg |
| 4. Sodium Alginate | 20 mg |
| 5. Mg stearate | 1.3 mg |

Procedure for Tablet Formulation

Ingredients 1, 2, 3 and 4 are blended in a suitable mixer/blender. Sufficient water is added portion-wise to the blend with careful mixing after each addition until the mass is of a consistency to permit its conversion to wet granules. The wet mass is converted to granules by passing it through an oscillating granulator using a No. 8 mesh (2.38 mm) screen. The wet granules are then dried in an oven at 140° F. (60° C.) until dry. The dry granules are lubricated with ingredient No. 5, and the lubricated granules are compressed on a suitable tablet press.

EXAMPLE 14

Parenteral Formulation

A pharmaceutical composition for parenteral administration is prepared by dissolving an appropriate amount of a compound of Formula I in polyethylene glycol with heating. This solution is then diluted with water for injections (to 100 mL). The solution is then rendered sterile by filtration through a 0.22 micron membrane filter and sealed in sterile containers.

All publications, including but not limited to patents and patent applications cited in this specification are herein incorporated by reference as if each individual publication were specifically and individually indicated to be incorporated by reference as though fully set forth.

What is claimed is:

1. A compound or salt selected from the group consisting of:
1,4-bis(2-phenylamino-4-thiazolyl)benzene,
1-[2-phenyl-4-(5-bromo)thiazolyl]-4-[2-phenyl-4-thiazolyl]benzene,
1,4-bis(2-phenylamino-4-(5-bromo)thiazolyl)benzene,
1,4-bis(2-(3-pyridylamino)-4-thiazolyl)benzene,
1,4-bis(2-phenyl)-(4-(5-bromo)thiazolyl)benzene,
1-[(2-(3-pyridylamino)-4-(5-bromo)thiazolyl)]-4-[2-(3-pyridylamino)-4-thiazolyl]benzene,
1,3-bis(2-(3-pyridylamino)-4-thiazolyl)benzene,
1,4-bis(2-(2-pyridylamino)-4-thiazolyl)benzene,
4,4'-di(2-(2-methoxypyrid-5-ylamino)thiazolyl),
4,4'-di(2-(2-pyridylamino)thiazolyl)dihydrobromide, and
1,4-bis(2-(3-pyridylamino)-4-thiazolyl)benzene bistrifluoroacetate.

2. A compound according to claim 1 selected from the group consisting of:
1,4-bis(2-phenylamino-4-thiazolyl)benzene,
1-[2-phenyl-4-(5-bromo)thiazolyl]-4-[2-phenyl-4-thiazolyl]benzene,
1,4-bis(2-phenylamino-4-(5-bromo)thiazolyl)benzene,
1,4-bis(2-(3-pyridylamino)-4-thiazolyl)benzene bistrifluoroacetate,
1-[(2-(3-pyridylamino)-4-(5-bromo)thiazolyl)]-4-[2-(3-pyridylamino)-4-thiazolyl]benzene,
1,3-bis(2-(3-pyridylamino)-4-thiazolyl)benzene,
4,4'-di(2-(2-methoxypyrid-5-ylamino)thiazolyl),
1,4-bis(2-(2-pyridylamino)-4-thiazolyl)benzene, and
4,4'-di(2-(2-pyridylamino)thiazolyl)dihydrobromide.

3. A compound according to claim 2 selected from the group consisting of:
1,4-bis(2-phenylamino-4-thiazolyl)benzene,
1-[2-phenyl-4-(5-bromo)thiazolyl]-4-[2-phenyl-4-thiazolyl]benzene,
1,4-bis(2-phenylamino-4-(5-bromo)thiazolyl)benzene,
1,4-bis(2-(3-pyridylamino)-4-thiazolyl)benzene,
1-[(2-(3-pyridylamino)-4-(5-bromo)thiazolyl)]-4-[2-(3-pyridylamino)-4-thiazolyl]benzene,
1,4-bis(2-(2-pyridylamino)-4-thiazolyl)benzene,
1,3-bis(2-(3-pyridylamino)-4-thiazolyl)benzene and
4,4'-di(2-(2-pyridylamino)thiazolyl)dihydrobromide.

4. A method of inhibiting myt1 kinase which comprises administering to a subject in need thereof, an effective amount of a compound according to claim 1.

5. A method of treating a disease or disorder selected from the group consisting of leukemia, soft tissue cancers, brain cancer, esophageal cancer, stomach cancer, pancreatic cancer, liver cancer, lung cancer, bladder cancer, bone cancer, prostate cancer, ovarian cancer, cervical cancer, uterine cancer, testicular cancer, kidney cancer, head cancer and neck cancer, chronic inflammatory proliferative diseases, proliferative cardiovascular diseases, prolifertive ocular disorders and benign hyperproliferative diseases which comprises administering to a subject in need thereof an effective amount of a compound according to claim 1.

6. A method according to claim 5 wherein the disease or disorder treated is selected from the group consisting of psoriasis, rheumatoid arthritis, diabetic retinopathy and hemangiomas.

* * * * *